(12) United States Patent
Wilkins et al.

(10) Patent No.: US 7,586,613 B2
(45) Date of Patent: Sep. 8, 2009

(54) METHOD FOR MEASUREMENT OF GAS CONCENTRATION WITH MODULATED LIGHT AT TWO ABSORPTION MAXIMA

(75) Inventors: Paul Wilkins, Vantaa (FI); Samuli Laukkanen, Rajamäki (FI)

(73) Assignee: Vaisala Oyj, Helsinki (FI)

( * ) Notice: Subject to any disclaimer, the term of this patent is extended or adjusted under 35 U.S.C. 154(b) by 0 days.

(21) Appl. No.: 11/662,899

(22) PCT Filed: Sep. 7, 2005

(86) PCT No.: PCT/FI2005/000383

§ 371 (c)(1),
(2), (4) Date: Apr. 23, 2007

(87) PCT Pub. No.: WO2006/030058

PCT Pub. Date: Mar. 23, 2006

(65) Prior Publication Data

US 2007/0295908 A1    Dec. 27, 2007

(30) Foreign Application Priority Data

Sep. 15, 2004    (FI) .................................. 20041197

(51) Int. Cl.
G01N 21/00    (2006.01)
(52) U.S. Cl. .................................. 356/437; 250/339.13
(58) Field of Classification Search .................. 356/437; 250/339.13
See application file for complete search history.

(56) References Cited

U.S. PATENT DOCUMENTS 5,317,156 A    5/1994   Cooper et al.
5,572,031 A    11/1996  Cooper et al.
5,636,035 A *  6/1997   Whittaker et al. ............ 356/437
5,930,000 A *  7/1999   Brand .......................... 356/437
5,973,782 A    10/1999  Bomse
6,522,402 B1 * 2/2003   Wang et al. .................. 356/327
6,875,399 B2 * 4/2005   McVey .......................... 422/3
7,304,742 B1 * 12/2007  Gurton ........................ 356/432
2006/0098202 A1* 5/2006  Willing et al. .............. 356/437

FOREIGN PATENT DOCUMENTS

WO    WO-02/090935 A2    11/2002

* cited by examiner

Primary Examiner—Gregory J Toatley, Jr.
Assistant Examiner—Rebecca C Slomski
(74) Attorney, Agent, or Firm—Birch, Stewart, Kolasch & Birch, LLP

(57) ABSTRACT

A method for improving optical measurement of gas concentration includes steps for directing narrow band light to the gas to be measured and measuring the attenuation of the light in the gas, modulating the center wavelength of the light source around or over a first predetermined absorption maximum (absorption line) of the measured gas and aside of it, measuring the attenuation of the light in the gas as a function of the center wavelength of the light, and determining the gas concentration based on the measurement. The center wavelength of the light is varied such that the center wavelength is adapted to coincide with at least one other absorption maximum (peak) with different absorption properties of the gas to be measured, and correspondingly the attenuation of the other absorption maximum or maxima is measured as a function of the center wavelength of the light.

14 Claims, 2 Drawing Sheets

METHOD FOR MEASUREMENT OF GAS CONCENTRATION WITH MODULATED LIGHT AT TWO ABSORPTION MAXIMA

CROSS-REFERENCE TO RELATED APPLICATION

The present application claims priority under 35 U.S.C. § 119 to Finnish Application No. 2004-1197, filed Sep. 15, 2004 and International Application No. PCT/FI2005/000383, filed Sep. 7, 2005, the entire contents of which are hereby incorporated by reference.

BACKGROUND OF THE INVENTION

1. Field of the Invention

The invention relates to a method for improving optical measurement of gas concentration.

2. Description of Background Art

In U.S. Pat. No. 5,527,031 is described an optical measurement method where a reference gas cell is used for the calibration and locking of the device on an oxygen absorption line. This method is rather complicated and is susceptible to changes in the measurement environment. WO 87/07018 describes a calibration method in connection with a oxygen concentration measurement device. In this method the wavelength of the emitting laser is scanned through a range of wavelengths that includes the absorption line.

U.S. Pat. No. 6,269,110 describes a calibration method for tunable ArF-excimer laser. In this solution the laser has a discharge chamber where a molecular species is introduced for calibration purposes.

U.S. Pat. No. 6,107,631 describes a self-calibration approach for tunable laser spectral absorption sensors. In this solution stored calibration information is used with current sensor reading information for calibration purposes.

SUMMARY AND OBJECTS OF THE INVENTION

It is an object of the present invention to overcome the drawbacks of the above-described techniques and to provide an entirely novel type of method for measuring improving optical measurement of gas concentration.

The goal of the invention is accomplished by varying the center wavelength of the light such that the center wavelength is adapted to coincide with at least two absorption maxima (peak) with different absorption properties of the gas to be measured, and correspondingly the attenuation of the other absorption maxima is measured as a function of the center wavelength of the light.

The invention offers significant benefits over conventional techniques.

The implantation of the invention is relatively simple.

The invention offers an effective two-point calibration in a single gas. Operating the TDL (Tunable Diode Laser) transmitter at a secondary absorption line (e.g. of lower strength) effectively simulates measurement of a lower concentration of oxygen. Due to the precise ratio of the strengths of any two absorption lines, at a given temperature and pressure, is a fundamental property of the oxygen absorption spectrum, and is a physical constant, the calibration is based on absolute accuracy. This fact offers the possibility to perform ratiometric measurements, using the ideal relationship between the strengths of two absorption lines as a reference, if the absolute absorption at only one line is known. In addition, the position (wavelength) of each individual line in the oxygen absorption spectrum is a physical constant. Knowledge of the position and separation of the lines in the spectrum may therefore be used to determine measurement parameters differentially, if a transmitter is operated at two or more lines. Thus, alternate operation at two or more lines yields significant additional measurement information, which is unavailable if only one absorption line is utilized.

Therefore, only one calibration gas is required to perform both offset and gain correction. This reduces calibration gas costs for the end-user, compared to a standard two-point calibration using two gases. In addition, the technique offers a more reliable single-gas calibration than a standard one-point field calibration. In certain field-calibration cases, this effective two-point calibration may be performed with an acceptable level of accuracy in ambient air.

This effective two-point calibration is applicable to both wall- and process-mounted type transmitters. Indeed, in production it may be possible to calibrate the wall-mounted transmitters in the station intended for in-situ process-mounted transmitters, despite the differences in the operational behaviour of the internal series reference path.

The invention offers self-diagnostic functions. Two-line operation offers the possibility to implement several valuable in-service self-diagnostic functions. These include: oxygen measurement accuracy verification; tunable laser wavelength current-tuning coefficient monitoring; absorption line operating point confirmation. These self-diagnostic functions are of particular benefit in monitoring long-term changes in laser characteristics, and cannot be implemented if only one absorption line is used. The importance of such self-diagnostic capabilities should be emphasised, given the safety-critical nature of many $O_2$ measuring applications.

The invention offers also self-adjustment. Operation at two absorption lines enables the transmitter to detect if the VCSEL current-tuning coefficient has changed over time. The laser's current modulation amplitude may then be adjusted, allowing the existing calibration coefficients to be applied more accurately to the aged laser characteristics.

There also exists the possibility for in-service correction of the measurement linearity, if the drift mechanism is predictable. Clearly, such a self-adjustment system would require rigorous long-term testing.

The two-line technique is mathematically simple. No complex algorithms or models are required. The additional data-processing requirements are minimal.

The invention requires no extra hardware compared with single wavelength absorption measurements.

The method has a fast operation. Due to the nature of current-controlled wavelength tuning, the two-line technique is very rapid. Interruption to the measurement reading is negligible.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following the invention is described in greater detail with the help of exemplifying embodiments illustrated in the appended drawings in which.

DETAILED DESCRIPTION OF THE PREFERRED EMBODIMENTS

Figure 1:
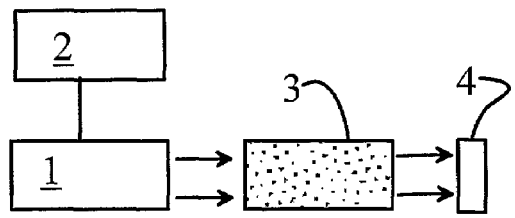
FIG. 1 shows a block diagram of a measuring system suitable for the method in accordance with the invention.

FIG. 1 shows a typical measurement system for oxygen concentration measurement. The system comprises a narrow-band light source 1, which could be e.g. Vertical Cavity Surface Emitting Laser (later VCSEL). The wavelength of this type of laser is typically controlled by current by an adjustable current source 2. The light emitted by the laser 1 is directed to a gas-permeable measurement chamber 3 and the attenuation caused by the gas in the chamber 3 is detected by a detector 4.

In other words in the measurement narrow-band light is directed to the gas to be measured and the attenuation of the light in the gas is measured. Typically the center wavelength of the light source 1 is modulated by the current source 2 around or over a first predetermined absorption maximum (absorption line) of the measured gas and aside of it and the attenuation of the light in the gas 3 as a function of the center wavelength of the light is measured and on the basis of this procedure the gas concentration is determined.

According to the invention the center wavelength of the light of the light source 1 is further varied such that the center wavelength is adapted to coincide with at least one other absorption maximum (peak) with different absorption properties of the gas, e.g. oxygen, to be measured, and correspondingly the attenuation of the other absorption maximum or maxima is measured as a function of the center wavelength of the light.

The two absorption line technique is described in the following in more detail.

The description begins with the theory of operation and is followed by the measurement results.

Theory of Two-Line Operation of a TDL Oxygen Transmitter

Figure 2:
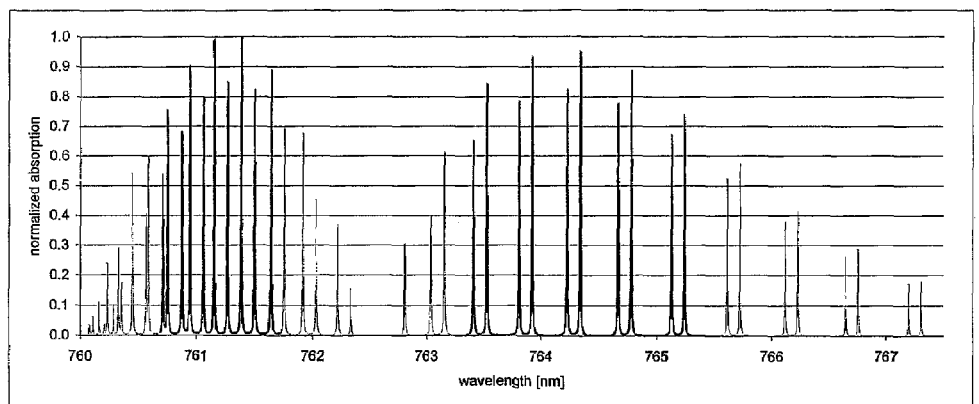
FIG. 2 is a graph illustrating $O_2$ absorption spectrum where absorption line pairs with a primary line having more than 60% of normalized absorption are shown in bold.

The absorption spectrum of oxygen between 760 nm and 767 nm is shown in FIG. 2. In order to maximise the absorption signal amplitude, as detected by the TDL oxygen transmitter, one of the strongest lines of the spectrum is selected as the primary operating line. As seen in the figure, all the strongest lines are accompanied by an adjacent line that has a significantly weaker absorption strength.

As an example of an application of two-line measurement, it will be shown that it is possible to perform an effective two-point calibration in a single gas. This may be achieved by measuring the $O_2$ absorption signals at both a primary and an adjacent line. Ideally, the ratio of the signal amplitudes detected by the transmitter will be the same as the ratio of the absorption strengths of the two lines. Knowing that ratio, and the concentration of the single calibration gas, the required calibration coefficients can be calculated. The average ratio of absorption strengths between the primary and adjacent lines shown in FIG. 2 is 0.85. In practice, this means that if the two-line calibration is performed in ambient conditions of 21% $O_2$, then the method effectively simulates a two-point calibration in concentrations of 21% $O_2$ and 16% $O_2$. However, due to the inherently linear absorption of $O_2$, this technique is able to provide a calibrated measurement that retains sufficient accuracy even when the transmitter is measuring low concentrations of oxygen.

Figure 3:
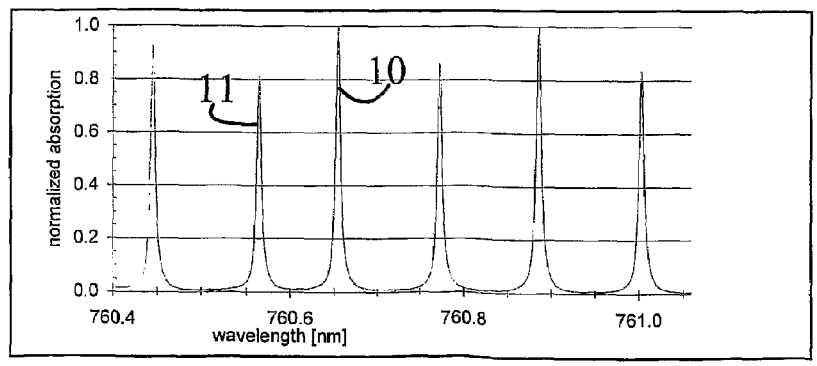
FIG. 3 is a graph illustrating an example of $O_2$ absorption lines covered by the linear operating range of a typical VCSEL, implementable according to the invention.
Figure 4:
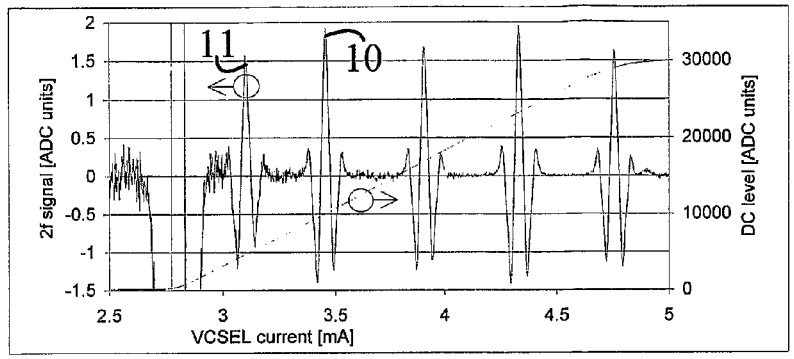
FIG. 4 is a graph illustrating measured corresponding $O_2$ signal amplitudes and linear tuning range obtainable according to the invention.

Of practical benefit is that the adjacent line is positioned well within the current tuning range of a typical VCSEL, when operating at the primary line. FIGS. 3 and 4 show a measured example of this. The linear tuning range of the VCSEL and measured $O_2$ signals are shown in FIG. 4, and the corresponding $O_2$ absorption lines in FIG. 3. A relatively small change in current of −0.5 mA is required to tune the laser wavelength between the primary line 10 and the adjacent line 11. A decrease in the measured signal peak-to-peak amplitude can readily be seen, in direct response to the weaker absorption strength of the adjacent line 11.

Test Results

Figure 5:
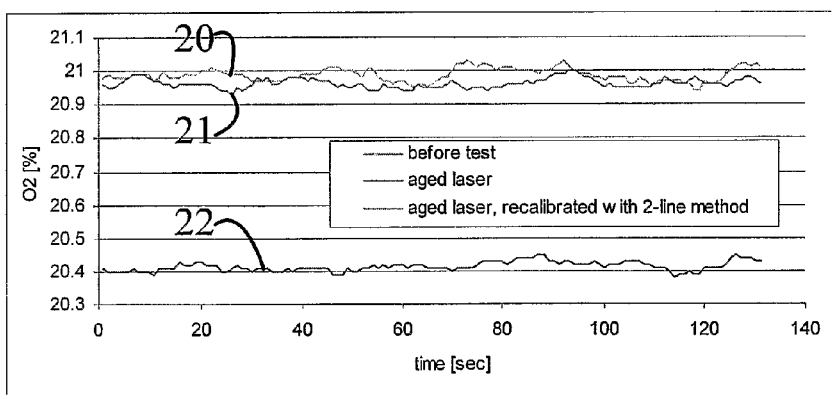
FIG. 5 is a graph illustrating first measured $O_2$ readings from a two-line recalibration test according to the invention.
Figure 6:
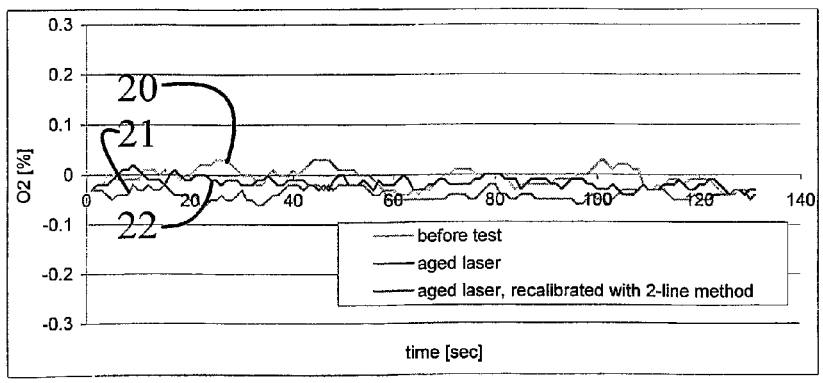
FIG. 6 is a graph illustrating second measured $O_2$ readings from a two-line recalibration test according to the invention.

The two-line calibration method was tested with a prototype TDL oxygen transmitter. Test results are shown in FIGS. 5 and 6. The initial response is shown as graph 20, and illustrates the $O_2$ measurement typically obtained from a calibrated transmitter. Ageing of the laser was then simulated by manually changing the current modulation amplitude, which in practice results in a condition where the tuning coefficient of the laser appears to have aged, and decreased by a factor of 30%. The effect of this simulated ageing on the $O_2$ measurement is shown as graph 22, and represents the response which may be obtained from a transmitter exhibiting measurement drift. In this case, a significant error is seen at the 20% $O_2$ region, whereas the measurement at zero has not changed. The "aged" transmitter was the recalibrated with the two-line method in a single gas, meaning in practice that both the offset and gain factors are resolved. The recalibration result is shown as graph 21. It can be seen that the calibration was successful.

In this instance, since the simulated tuning coefficient ageing is a phenomenon which affects only the gain of the measurement, the zero reading of the "aged" transmitter is still accurate prior to recalibration. However, it should be emphasised that the two-line recalibration recalculates both the offset and the gain factors of the measurement. The method is therefore capable of recalibrating a transmitter with simultaneous gain and offset errors by using only single gas.

Alternative Embodiments

The system performance may be improved further by defining during calibration procedure the light source 1 control signals, which are required to vary the wavelength to the said first absorption maximum 10 and said other absorption maxima 11, and by using the defined properties of the light source control signals and/or the attenuation information of other absorption maxima for calculations improving the quality of the gas concentration measurement.

According to the other embodiments of the invention the following additional features may be used:

The narrow-band light is advantageously essentially monochromatic.

The light source 1 is advantageously an adjustable diode laser or quantum cascade laser.

The measured properties of the other absorption maxima 11 are in one preferred embodiment used for calibration or adjustment of the gas concentration indicated by the measurement device.

The measured properties of the other absorption maxima 11 are in another preferred embodiment used for gas temperature measurement and consequent temperature correction of the indication of the measurement device.

The measured properties of the other absorption maxima 11 are in another preferred embodiment are used for self-diagnostic checking of the device.

The measured properties of the other absorption maxima 11 are in another preferred embodiment used for determining the wavelength tuning coefficients of the diode laser 1.

The measured properties of the other absorption maxima 11 are in another preferred embodiment used for determining or verifying the center wavelength of the light emitted by the light source 1.

The measured properties of the other absorption maxima 11 are in another preferred embodiment are used for determining other properties of the light source 1.

It is typical for the invention that at least one of the other absorption maxima 11 of the gas is adjacent to the first absorption maximum 10.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method for self-diagnostic checking or self-adjustment of an optical gas concentration measurement device, the method comprising steps for
    directing narrow-band light to gas to be measured and measuring attenuation of the light in the gas,
    modulating a center wavelength of the light source around or over a first predetermined absorption maximum (10) (absorption line) of the measured gas,
    measuring the attenuation of the light in the gas as a function of the center wavelength of the light,
    determining gas concentration based on the measurement,
    varying the center wavelength of the light such that the center wavelength is adapted to coincide with at least one other absorption maximum (11) (peak) with different absorption properties of the gas to be measured,—
    measuring correspondingly the attenuation of the other absorption maximum or maxima (11) as a function of the center wavelength of the light,
    defining the light source (1) control signals required to vary the wavelength to the said first absorption maximum and said other absorption maxima, and
    using the defined properties of the light source control signals and/or measured attenuation information of said other absorption maxima for self-diagnostic checking of the device.

2. A method according to claim 1, wherein the narrow band light is essentially monochromatic.

3. A method according to claim 2,
    further comprising the step of obtaining the light from an adjustable diode laser or quantum cascade laser (1).

4. A method according to claim 1,
    further comprising the step of using the measured properties of the other absorption maxima (11) for calibration or adjustment of the gas concentration indicated by the measurement device.

5. A method according to claim 1,
    further comprising the step of using the measured properties of the other absorption maxima (11) for gas temperature measurement and consequent temperature correction of the indication of the measurement device.

6. A method according to claim 1,
    further comprising the step of using the measured properties of the other absorption maxima (11) for determining the wavelength tuning coefficients of the diode laser.

7. A method according to claim 1,
    further comprising the step of using the measured properties of the other absorption maxima (11) for determining or verifying the center wavelength of the light emitted by the light source.

8. A method according to claim 1,
    further comprising the step of using the measured properties of the other absorption maxima (11) for determining other properties of the light source.

9. A method according to claim 1, at least one of the other absorption maxima (11) of the gas is adjacent to the first absorption maximum (10).

10. A method for self-diagnostic checking or self-adjustment of an optical gas concentration measurement device, the method comprising steps for
    directing narrow-band light to gas to be measured and measuring attenuation of the light in the gas,
    modulating a center wavelength of the light source around or over a first predetermined absorption maximum (10) (absorption line) of the measured gas,
    measuring the attenuation of the light in the gas as a function of the center wavelength of the light,
    determining gas concentration based on the measurement,
    varying the center wavelength of the light such that the center wavelength is adapted to coincide with at least one other absorption maximum (11) (peak) with different absorption properties of the gas to be measured,
    measuring correspondingly the attenuation of the other absorption maximum or maxima (11) as a function of the center wavelength of the light,
    defining the light source (1) control signals required to vary the wavelength to the said first absorption maximum and said other absorption maxima, and
    using measured attenuation information of said other absorption maxima for self-diagnostic checking of the device.

11. A method for self-diagnostic checking or self-adjustment of an optical gas concentration measurement device, the method comprising steps for
    directing narrow-band light to a gas to be measured and measuring attenuation of the light in the gas,
    modulating a center wavelength of the light source around or over a first predetermined absorption maximum (10) (absorption line) of the measured gas,
    measuring the attenuation of the light in the gas as a function of the center wavelength of the light,
    determining gas concentration based on the measurement,
    varying the center wavelength of the light such that the center wavelength is adapted to coincide with at least one other absorption maximum (11) (peak) with different absorption properties of the gas to be measured,
    measuring correspondingly the attenuation of the other absorption maximum or maxima (11) as a function of the center wavelength of the light,
    defining the light source (1) control signals required to vary the wavelength to the said first absorption maximum and said other absorption maxima, and
    using the defined properties of the light source control signals for self-diagnostic checking of the device.

12. A method according to claim 1, wherein the device includes only a single gas chamber, and the step of measuring the attenuation of the light in the gas is performed in the single gas chamber.

13. A method according to claim 1, wherein the step of modulating the center wavelength of the light source around or over a first predetermined absorption maximum (10) (absorption line) of the measured gas is performed by manually changing a current modulation amplitude in order to cause a tuning coefficient of the light source to appear to be aged.

14. A method according to claim 4, wherein the gas is a single gas, and
wherein the method is capable of recalibrating the device with simultaneous gain and offset errors by using only the single gas.

\* \* \* \* \*